United States Patent
Lee et al.

(10) Patent No.: US 9,200,019 B2
(45) Date of Patent: Dec. 1, 2015

(54) PHOSPHORUS 2-PYRONE DERIVATIVE AND PREPARATION METHOD THEREOF

(71) Applicant: KNU-INDUSTRY COOPERATION FOUNDATION, Chuncheon-si, Gangwon-do (KR)

(72) Inventors: Phil Ho Lee, Chuncheon-si (KR); Jun tae Mo, Chuncheon-si (KR); Taekyu Ryu, Chuncheon-si (KR)

(73) Assignee: Knu-Industry Cooperation Foundation, Chuncheon-si, Gangwon-do (KR)

( * ) Notice: Subject to any disclaimer, the term of this patent is extended or adjusted under 35 U.S.C. 154(b) by 0 days.

(21) Appl. No.: 14/411,020

(22) PCT Filed: Jun. 27, 2013

(86) PCT No.: PCT/KR2013/005724
§ 371 (c)(1),
(2) Date: Dec. 23, 2014

(87) PCT Pub. No.: WO2014/003467
PCT Pub. Date: Jan. 3, 2014

(65) Prior Publication Data
US 2015/0191497 A1 Jul. 9, 2015

(30) Foreign Application Priority Data

Jun. 28, 2012 (KR) .................. 10-2012-0069729

(51) Int. Cl.
| | |
|---|---|
| *C07F 9/655* | (2006.01) |
| *C07F 9/40* | (2006.01) |
| *B01J 23/52* | (2006.01) |
| *C07F 9/6571* | (2006.01) |

(52) U.S. Cl.
CPC .............. *C07F 9/6552* (2013.01); *B01J 23/52* (2013.01); *C07F 9/4015* (2013.01); *C07F 9/4078* (2013.01); *C07F 9/657181* (2013.01)

(58) Field of Classification Search
USPC ..................................................... 558/82, 214
See application file for complete search history.

(56) References Cited

PUBLICATIONS

Mo et al., Gold-Catalyzed Sequential Alkyne Activation for the Synthesis of 4,6-Disubstituted Phosphorus 2-Pyrones, 2013, Organic Letters, vol. 15, No. 1, 26-29.*
Trishin et al., Reactions of dialkyl esters of alkynylphosphonous acids with bromoacetone and alpha-bromoacetophenone, 1989, Doklady Akademii Nauk SSSR, 304(3), 625-9.*
Polozov, Alexandre M. et al, "Synthesis of 2H-1, 2-oxaphosphorin 2-oxides." Journal of Organometallic Chemistry, vol. 646, No. 1, Mar. 2002, pp. 153-160.
Peng, Ai-Yun et al., "Synthesis of 2 H-1, 2-Oxaphosphorin 2-Oxides via Ag2CO3-Catalyzed Cyclization of (Z)-2-Alken-4-ynylphosphonic Monoesters" Organic Letters vol. 7, No. 15, Jun. 24, 2005, pp. 3299-3301.
Zhao, Jing et al., "Synthesis of Aromatic Ketones by a Transition Metal-Catalyzed Tandem Sequence", Journal of the American Chemical Society, vol. 128, No. 23, May 17, 2006, pp. 7436-7437.
Luo, Tuoping, et al. "Syntheses of α-Pyrones Using Gold-Catalyzed Coupling Reactions." Organic Letters, vol. 13, No. 11, May 2, 2011, No. 2834-2836.

* cited by examiner

*Primary Examiner* — Kristin Vajda
(74) *Attorney, Agent, or Firm* — Alleman Hall McCoy Russell & Tuttle LLP

(57) ABSTRACT

Provided are a novel phosphorus 2-pyrone derivative and a preparation method thereof. The phosphorus 2-pyrone derivative according to the present invention is capable of being efficiently synthesized by treating an alkyl hydrogen alkynylphosphonate derivative and an alkyne derivative with a minimal amount of a gold catalyst.

10 Claims, No Drawings

PHOSPHORUS 2-PYRONE DERIVATIVE AND PREPARATION METHOD THEREOF

CROSS REFERENCE TO RELATED APPLICATIONS

The present application is a U.S. National Phase of International Patent Application Serial No. PCT/KR2013/005724, entitled "NOVEL PHOSPHOROUS 2-PYRONE DERIVATIVE AND PREPARATION METHOD THEREOF," filed on Jun. 27, 2013, which claims priority to Korean Patent Application No. 10-2012-0069729, entitled "NOVEL PHOSPHOROUS 2-PYRONE DERIVATIVE AND PREPARATION METHOD THEREOF," filed on Jun. 28, 2012, the entire contents of each of which are hereby incorporated by reference for all purposes.

TECHNICAL FIELD

The present invention relates to a novel phosphorus 2-pyrone derivative and a preparation method thereof, and more specifically, to a method of efficiently synthesizing a phosphorus 2-pyrone derivative by treating an alkyl hydrogen alkynylphosphonate derivative and an alkyne derivative with a minimal amount of a gold (Au) catalyst.

BACKGROUND ART 2-pyrone is a natural material used as a synthetic intermediate for various materials and having biological activity. It has recently become known that 2-pyrone derivatives have an HIV-inhibiting activity and as a result, 2-pyrone derivatives are receiving a lot of attention.

Phosphorus 2-pyrone derivatives are similar to the 2-pyrone derivatives in view of a structure of the biological properties. However, there are only 4 known methods of synthesizing the phosphorus 2-pyrone derivatives so far, and known structures of the derivatives are also extremely limited (*Org. Lett.* 2005, 7, 3299). Accordingly, in order to develop a reaction for efficiently synthesizing various phosphorus 2-pyrone derivatives, the present inventors developed a catalytic reaction using a gold (Au) catalyst to efficiently synthesize the phosphorus 2-pyrone derivatives including various structures.

DISCLOSURE

Technical Problem

An object of the present invention is to provide a novel phosphorus 2-pyrone derivative and a preparation method thereof.

In addition, another object of the present invention is to provide an intermediate compound for preparing the phosphorus 2-pyrone derivative and a preparation method thereof.

Technical Solution

In one general aspect, there are provided a novel phosphorus 2-pyrone derivative represented by the following Chemical Formula 1, and a preparation method thereof:

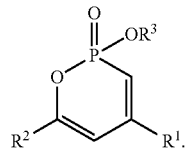

[Chemical Formula 1]

In another general aspect, there are provided an alkyl alkenyl alkynyl phosphonate derivative represented by the following Chemical Formula 2 which is an intermediate compound for preparing the phosphorus 2-pyrone derivative, and a preparation method thereof:

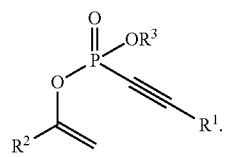

[Chemical Formula 2]

Hereinafter, the present invention will be described in detail.

Here, unless technical and scientific terms used herein are defined otherwise, they have meanings generally understood by those skilled in the art to which the present invention pertains. In addition, repeated descriptions for technical constitution and function as the same as the related art will be omitted.

The present invention provides a phosphorus 2-pyrone derivative represented by the following Chemical Formula 1:

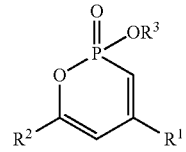

[Chemical Formula 1]

in Chemical Formula 1, $R^1$ is (C1-C7)alkyl or (C6-C20)aryl;
$R^2$ is (C1-C7)alkyl, (C3-C12)cycloalkyl, (C6-C20)aryl, (C3-C12)cycloalkenyl or (C6-C20)ar(C1-C7)alkyl;
$R^3$ is (C1-C7)alkyl; and
the alkyl and the aryl of $R^1$ and $R^2$ may be further substituted with one or more selected from the group consisting of halogen, (C1-C7)alkyl, halo(C1-C7)alkyl, (C3-C12)cycloalkyl and (C1-C7)alkylcarbonyloxy.

In Chemical Formula 1 above, the 'alkyl' includes all of the linear or branched carbon chains, and examples of the 'aryl' may include phenyl, biphenyl, naphthyl, anthryl, and the like.

Specifically, in Chemical Formula 1 above, $R^1$ is n-butyl, n-pentyl, phenyl, 4-methylphenyl, 4-chlorophenyl or 4-trifluoromethylphenyl; $R^2$ is n-butyl, n-pentyl, 1-bromoethyl, 1-chloropropyl, cyclohexyl, cyclohexenyl, phenyl, 4-methylphenyl, 4-chlorophenyl, 4-trifluoromethylphenyl, 1-phenylethyl, 1-phenylpropyl, methylcarbonyloxymethyl, benzyl or cyclohexylmethyl; and $R^3$ is methyl, ethyl, propyl, butyl, pentyl, hexyl or heptyl.

More specifically, the phosphorus 2-pyrone derivative represented by Chemical Formula 1 above may be selected from the following compounds:

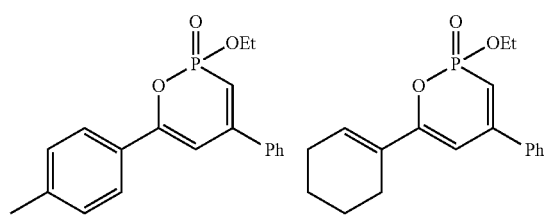
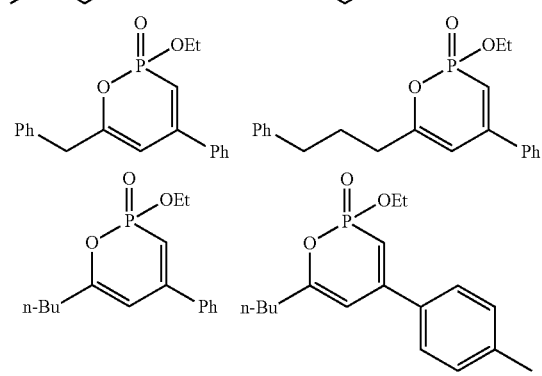

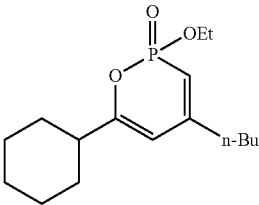
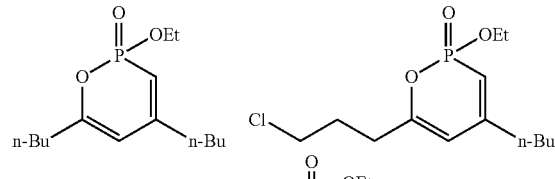
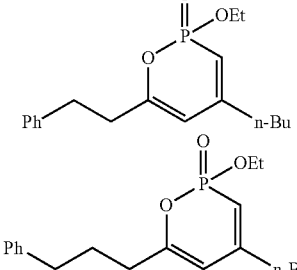
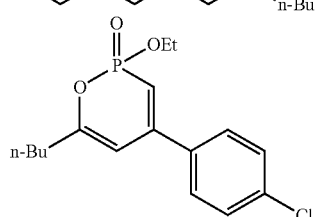
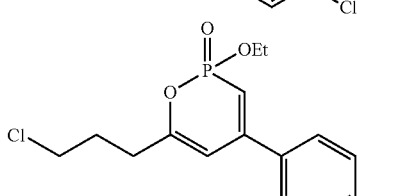
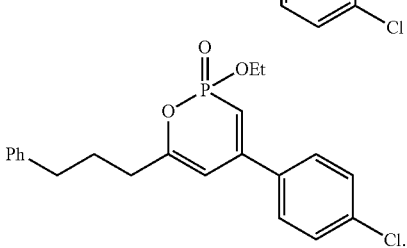

In addition, the present invention provides an alkyl alkenyl alkynyl phosphonate derivative represented by the following Chemical Formula 2, wherein the alkyl alkenyl alkynyl phosphonate derivative represented by the following Chemical Formula 2 is an intermediate for preparing the phosphorus 2-pyrone derivative represented by Chemical Formula 1:

[Chemical Formula 2]

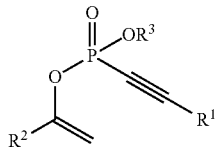

in Chemical Formula 2, $R^1$ is (C1-C7)alkyl or (C6-C20)aryl; $R^2$ is (C1-C7)alkyl, (C3-C12)cycloalkyl, (C6-C20)aryl, (C3-C12)cycloalkenyl or (C6-C20)ar(C1-C7)alkyl;

$R^3$ is a (C1-C7)alkyl; and the alkyl and the aryl of $R^1$ and $R^2$ may be further substituted with one or more selected from the group consisting of halogen, (C1-C7)alkyl, halo(C1-C7)alkyl, (C3-C12)cycloalkyl and (C1-C7)alkylcarbonyloxy.

Specifically, in Chemical Formula 2 above, $R^1$ is n-butyl, n-pentyl, phenyl, 4-methylphenyl, 4-chlorophenyl or 4-trifluoromethylphenyl; $R^2$ is n-butyl, n-pentyl, 1-bromoethyl, 1-chloropropyl, cyclohexyl, cyclohexenyl, phenyl, 4-methylphenyl, 4-chlorophenyl, 4-trifluoromethylphenyl, 1-phenylethyl, 1-phenylpropyl, methylcarbonyloxymethyl, benzyl or cyclohexylmethyl; and $R^3$ is methyl, ethyl, propyl, butyl, pentyl, hexyl or heptyl.

More specifically, the alkyl alkenyl alkynylphosphonate derivative may be selected from the following compounds:

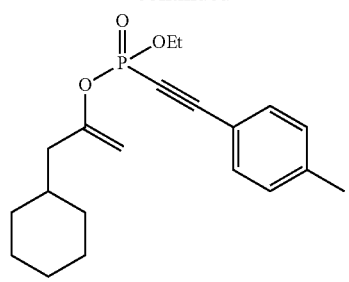

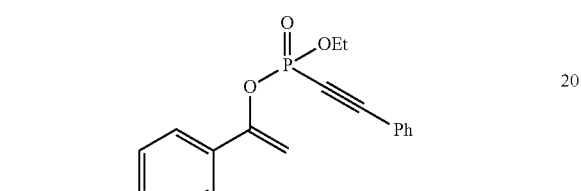

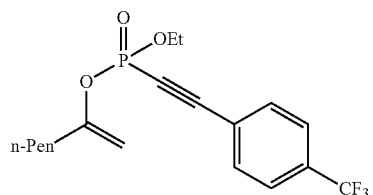

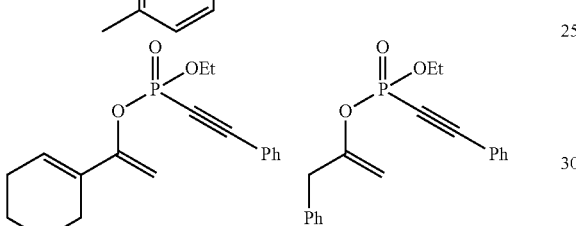

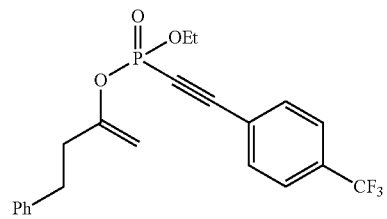

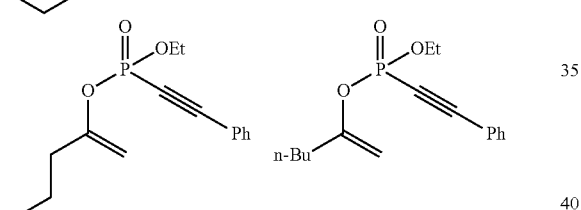

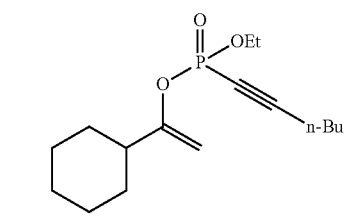

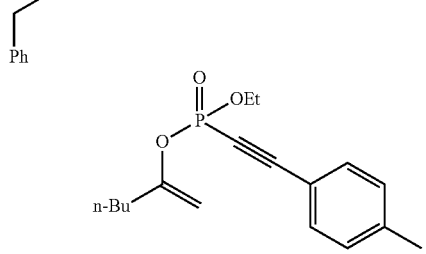

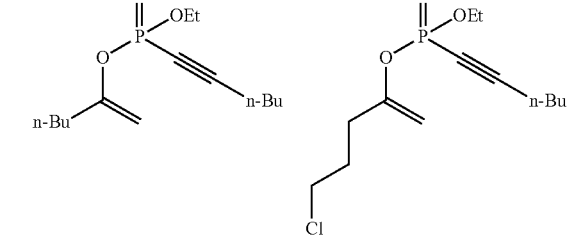

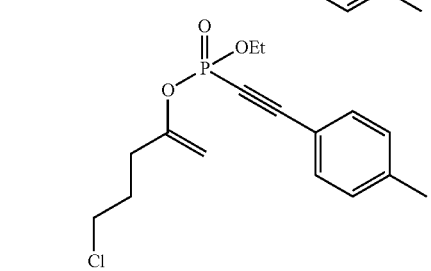

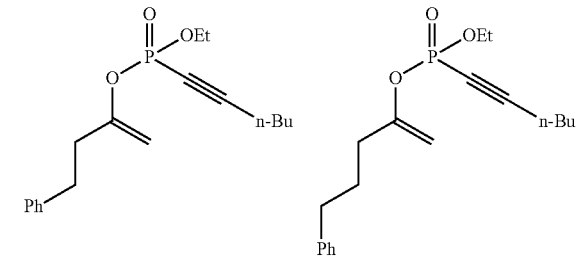

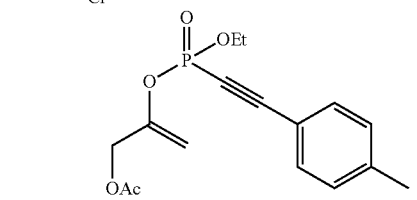

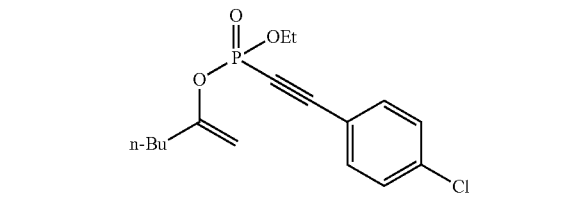

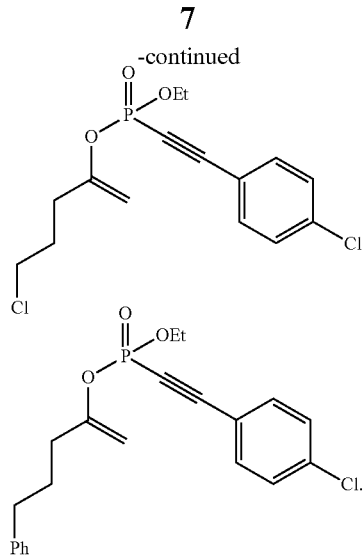

Further, the present invention provides a preparation method of a phosphorus 2-pyrone derivative represented by the following Chemical Formula 1 by reacting an alkyl hydrogen alkynyl phosphonate derivative represented by the following Chemical Formula 3 and an alkyne derivative represented by the following Chemical Formula 4 in the presence of a gold catalyst:

[Chemical Formula 1]
[Chemical Formula 3]
[Chemical Formula 4]

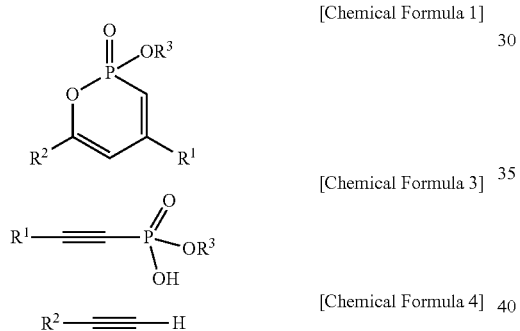

in Chemical Formulas 1, 3 and 4, $R^1$ is (C1-C7)alkyl or (C6-C20)aryl;

$R^2$ is (C1-C7)alkyl, (C3-C12)cycloalkyl, (C6-C20)aryl, (C3-C12)cycloalkenyl or (C6-C20)ar(C1-C7)alkyl;

$R^3$ is a (C1-C7)alkyl; and the alkyl and the aryl of $R^1$ and $R^2$ may be further substituted with one or more selected from the group consisting of halogen, (C1-C7)alkyl, halo(C1-C7)alkyl, (C3-C12)cycloalkyl and (C1-C7)alkylcarbonyloxy.

More specifically, the phosphorus 2-pyrone derivative represented by Chemical Formula 1 above may be prepared through the intermediate represented by Chemical Formula 2 by reacting various alkyl hydrogen alkynyl phosphonate derivatives represented by the following Chemical Formula 3 and the alkyne derivative represented by the following Chemical Formula 4 in the presence of the gold catalyst: (Reaction Formula 1)

[Reaction Formula 1]

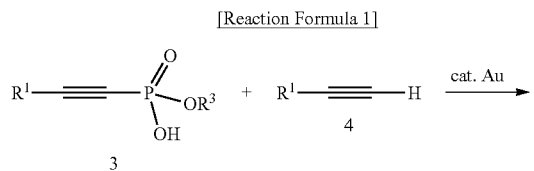

In addition, the phosphorus 2-pyrone derivative represented by Chemical Formula 1 above may be prepared by 1) a step of reacting the alkyl hydrogen alkynyl phosphonate derivative represented by Chemical Formula 3 above and the alkyne derivative represented by Chemical Formula 4 above in the presence of the gold catalyst and a base to prepare the alkyl alkenyl alkynyl phosphonate derivative represented by Chemical Formula 2 above; and 2) a step of performing an intramolecular cyclization reaction on the prepared alkyl alkenyl alkynyl phosphonate derivative represented by Chemical Formula 2 above in the presence of the gold catalyst to prepare the phosphorus 2-pyrone derivative represented by Chemical Formula 1 above: (Reaction Formula 2)

[Reaction Formula 2]

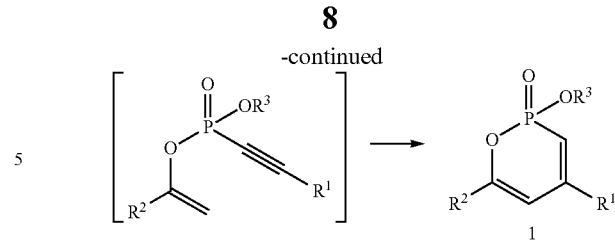

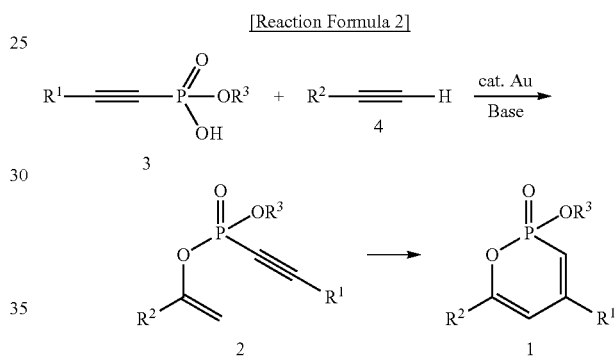

As a reaction container used in the preparation method of the present invention, a v-bial, a test tube, or a round flask may be used.

The gold (Au) catalyst used in the preparation method of the present invention may be one or more selected from the group consisting of AuCl, AuBr, AuCl$_3$, Ph$_3$PAuCl, (C$_6$F$_5$)$_3$PAuCl, (4-CF$_3$—C$_6$H$_4$)$_3$PAuCl, IMesAuCl [IMes: 1,3-bis(2,4,6-trimethylphenyl)imidazol-2-ylidene], IPrAuCl [IPr: 1,3-bis(2,6-diisopropylphenyl)imidazol-2-ylidene], Au(JohnPhos)Cl [JohnPhos:(2-biphenyl)di-tert-butylphosphine] and {[Au(JohnPhos)NCCH$_3$]$^+$SbF$_6$—}, and {[Au(JohnPhos)NCCH$_3$]$^+$SbF$_6$—} is the most preferred. The gold (Au) catalyst used in the preparation method of the present invention may be preferably used in 0.01 to 0.1 mol, and the most preferably, in 0.05 mol, based on 1 mol of the alkyl hydrogen alkynyl phosphonate derivative represented by Chemical Formula 3 above. In addition, the gold (Au) catalyst used in step 2) of Reaction Formula 2 above may be preferably used in 0.01 to 0.1 mol, and the most preferably, in 0.05 mol, based on 1 mol of the alkyl alkenyl alkynyl phosphonate derivative represented by Chemical Formula 2 above.

The solvent used in the preparation method (Reaction Formulas 1 and 2) of the present invention is general organic solvents. Preferably, at least one kind selected from the group consisting of dichloromethane (DCM), dichloroethane (DCE), toluene, acetonitrile (MeCN), nitromethane, tetrahydrofuran (THF), N,N-dimethylformamide (DMF) and N,N-dimethylacetamide (DMA) may be used as the solvent, and more preferably, dichloroethane (DCE) may be used as the solvent.

The reaction may be performed at a reaction temperature ranging from 20 to 40° C., or may be performed at room temperature to 30° C. The reaction time may be different according to reaction materials, kinds of catalysts, and an amount of starting materials. The reaction is allowed to be completed after confirming complete consumption of the alkyl hydrogen alkynyl phosphonate derivative which is a starting material, by TLC, or the like. When the reaction is completed, an extraction process is performed, then the solvent is distilled under reduced pressure, and a target material may be separated and purified by general methods such as column chromatography, and the like.

ADVANTAGEOUS EFFECTS

Phosphorus 2-pyrone derivatives according to the present invention may be used as a basic framework of natural materials having biological activity and may be developed as new types of drug or various pharmaceutical products.

In addition, with a preparation method of the phosphorus 2-pyrone derivative according to the present invention, the phosphorus 2-pyrone derivative may be efficiently prepared by an intermolecular addition reaction and a subsequent intramolecular cyclization reaction between a alkyl hydrogen alkynyl phosphonate derivative and an alkyne derivative in the presence of a gold (Au) catalyst.

BEST MODE

Hereinafter, the present invention will be described in detail with reference to examples. These examples are provided to help understand the present invention, and the scope of the present invention is not construed to be limited to these examples.

EXAMPLE 1

Preparation of 2-ethoxy-4-phenyl-6-p-methylphenyl-1,2-oxaphosphorin 2-oxide

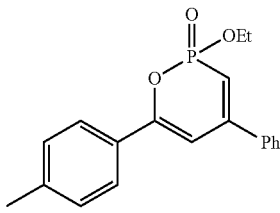 [SMILES: CCOP1(=O)C=C(c2ccccc2)C=C(c2ccc(C)cc2)O1]

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was added thereto. After stirring at room temperature for 5 minutes, ethyl hydrogen phenylethynylphosphonate (63.0 mg, 0.3 mmol) diluted with 0.5 mL of dichloroethane was added thereto. Then 1-ethynyl-4-methylbenzene (174 mg, 1.5 mmol) was put thereinto, followed by stirring at 30° C. for 16 hours, and when all of the starting materials disappeared in the TLC, the reaction was allowed to be completed. After the solvent was removed under low atmospheric pressure, the product was separated by chromatography to obtain 2-ethoxy-4-phenyl-6-p-methylphenyl-1,2-oxaphosphorin 2-oxide (33.2 mg, 34%) which is a title compound.

$^1$H NMR (400 MHz, CDCl$_3$) δ 7.69 (d, J=8.3 Hz, 2H), 7.57-7.54 (m, 2H), 7.46-7.44 (m, 3H), 7.24 (d, J=17.6 Hz, 2H), 6.54 (s, 1H), 6.04 (d, J=17.6 Hz, 1H), 4.26-4.22 (m, 2H), 2.40 (s, 3H), 1.39 (t, J=7.0 Hz, 3H).

EXAMPLE 2

Preparation of 2-ethoxy-4-phenyl-6-1-cyclohexenyl-1,2-oxaphosphorin 2-oxide

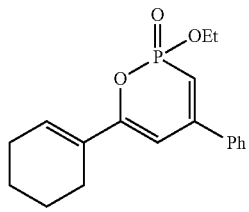 [SMILES: CCOP1(=O)C=C(c2ccccc2)C=C(C2=CCCCC2)O1]

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was added thereto. After stirring at room temperature for 5 minutes, ethyl hydrogen phenylethynylphosphonate (63.0 mg, 0.3 mmol) diluted with 0.5 mL of dichloroethane was added thereto. Then 1-ethynylcyclohex-1-ene (63.6 mg, 0.6 mmol) was put thereinto, followed by stirring at 30° C. for 18 hours, and when all of the starting materials disappeared in the TLC, the reaction was allowed to be completed. After the solvent was removed under low atmospheric pressure, the product was separated by chromatography to obtain 2-ethoxy-4-phenyl-6-1-cyclohexenyl-1,2-oxaphosphorin 2-oxide (58.8 mg, 62%) which is a title compound.

$^1$H NMR (400 MHz, CDCl$_3$) δ 7.50-7.43 (m, 2H), 7.43-7.41 (m, 3H), 6.73 (s, 1H), 5.98 (d, J=17.2 Hz, 1H), 5.92 (s, 1H), 4.23-4.15 (m, 2H), 2.26-2.21 (m, 4H), 1.75-1.62 (m, 4H), 1.38 (t, J=7.1 Hz, 3H).

EXAMPLE 3

Preparation of ethyl 3-phenylprop-1-en-2-yl phenylethynylphosphonate

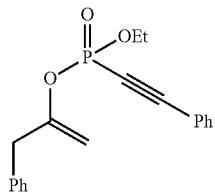

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) and triethylamine (Et$_3$N) (3.0 mg, 0.03 mmol) were put into a reaction container, and dichloroethane (0.4 mL) was put thereinto. After stirring at room temperature for 5 minutes, ethyl hydrogen phenylethynylphosphonate (63.0 mg, 0.3 mmol) diluted with 0.5 mL of dichloroethane was added thereto, and finally, prop-2-ynylbenzene (70 mg, 0.6 mmol) was put thereinto. Then, when all of the starting materials disappeared in the TLC, the reaction was allowed to be completed. After the solvent was removed under low atmospheric pressure, the product was separated by chromatography to obtain ethyl 3-phenylprop-1-en-2-yl phenylethynylphosphonate (68.9 mg, 71%) which is a title compound.

$^1$H NMR (400 MHz, CDCl$_3$) δ 7.54 (d, J=7.1 Hz, 2H), 7.54-7.45 (m, 1H), 7.40-7.29 (m, 2H), 7.28-7.24 (m, 5H), 5.06 (t, J=2.2 Hz, 1H), 4.56 (s, 1H), 4.21-4.13 (m, 2H), 3.58 (s, 2H), 1.36(t, J=7.0 Hz, 3H).

EXAMPLE 4

Preparation of 2-ethoxy-4-phenyl-6-benzyl-1,2-oxaphosphorin 2-oxide

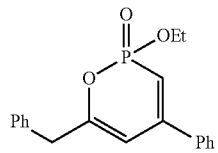 [SMILES: CCOP1(=O)C=C(c2ccccc2)C=C(Cc2ccccc2)O1]

Method 1—A gold (Ag(I)) catalyst {[Au(JohnPhos)NCCH$_3$]$^+$SbF$_6$—} [JohnPhos:(2-biphenyl)di-tent-butylphosphine] (11.3 mg, 0.015 mmol) was put into a reaction container, and dichloroethane (0.4 mL) was put thereinto. After stirring at room temperature for 5 minutes, ethyl 3-phenylprop-1en-2-yl phenylethynylphosphonate (example 3, 98 mg, 0.3 mmol) was put thereinto, and when all of the starting materials disappeared in the TLC, the reaction was allowed to be completed. After the solvent was removed under low atmospheric pressure, the product was separated by chromatography to obtain 2-ethoxy-4-phenyl-6-benzyl-1,2-oxaphosphorin 2-oxide (84.1 mg, 86%) which is a title compound.

Method 2—A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen phenylethynylphosphonate (63.0 mg, 0.3 mmol) diluted with 0.5 mL of dichloroethane was added thereto, and finally, prop-2-ynylbenzene (70 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-phenyl-6-benzyl-1,2-oxaphosphorin 2-oxide (68.5 mg, 70%) which is a title compound.

$^1$H NMR (400 MHz, CDCl$_3$) δ 7.43-7.39 (m, 5H), 7.34-7.26 (m, 5H), 5.92 (d, J=17.6 Hz, 1H), 5.84 (s, 1H), 4.03-3.94 (m, 2H), 3.71 (s, 2H), 1.19 (t, J=7.1 Hz, 3H).

EXAMPLE 5

Preparation of ethyl 5-Phenylpent-1-en-2-yl phenylethynylphosphonate

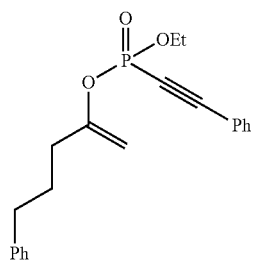 [SMILES: C=C(CCCc1ccccc1)OP(=O)(C#Cc1ccccc1)OCC]

A gold (Ag(I)) catalyst {[Au(JohnPhos)NCCH$_3$]$^|$SbF$_6$—} [JohnPhos:(2-biphenyl)di-tert-butylphosphine] (11.3 mg, 0.015 mmol) and triethylamine (Et$_3$N) (3.0 mg, 0.03 mmol) were put into a reaction container, and dichloroethane (0.4 mL) was put thereinto. After stirring at room temperature for 5 minutes, ethyl hydrogen phenylethynylphosphonate) (63.0 mg, 0.3 mmol) diluted with 0.5 mL of dichloroethane was added thereto, and finally, pent-4-ynylbenzene (86.5 mg, 0.6 mmol) was put thereinto. Then, when all of the starting materials disappeared in the TLC, the reaction was allowed to be completed. After the solvent was removed under low atmospheric pressure, the product was separated by chromatography to obtain ethyl 5-phenylpent-1-en-2-yl phenylethynylphosphonate (78.7 mg, 74%) which is a title compound.

$^1$H NMR (400 MHz, CDCl$_3$) δ 7.54-7.52 (m, 2H), 7.47-7.43 (m, 1H), 7.38-7.34 (m, 2H), 7.28-7.24 (m, 2H), 7.19-7.16 (m, 3H), 5.00 (t, J=2.2 Hz, 1H), 4.61-4.60 (m, 1H), 4.31-4.24 (m, 2H), 2.67 (t, J=7.6, 2H), 2.30 (t, J=7.4 Hz, 2H), 1.93-1.86 (m, 2H), 1.42 (t, J=7.0 Hz, 3H).

EXAMPLE 6

Preparation of 2-ethoxy-4-phenyl-6-3-phenylpropyl-1,2-oxaphosphorin 2-oxide

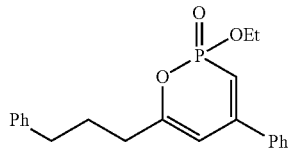

Method 1—A gold (Ag(I)) catalyst {[Au(JohnPhos)NCCH$_3$]$^+$SbF$_6$—} [JohnPhos:(2-biphenyl)di-tent-butylphosphine] (11.3 mg, 0.015 mmol) was put into a reaction container, and dichloroethane (0.4 mL) was put thereinto. After stirring at room temperature for 5 minutes, ethyl 5-phenylpent-1-en-2-yl phenylethynylphosphonate (Example 5, 106.3 mg, 0.3 mmol) was put thereinto, and when all of the starting materials disappeared in the TLC, the reaction was allowed to be completed. After the solvent was removed under low atmospheric pressure, the product was separated by chromatography to obtain 2-ethoxy-4-phenyl-6-3-phenylpropyl-1,2-oxaphosphorin 2-oxide (89.3 mg, 84%) which is a title compound.

Method 2—A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen phenylethynylphosphonate (63.0 mg, 0.3 mmol) diluted with 0.5 mL of dichloroethane was added thereto, and finally, pent-4-ynylbenzene (86.5 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-phenyl-6-3-phenylpropyl-1,2-oxaphosphorin 2-oxide (72.3 mg, 68%) which is a title compound.

$^1$H NMR (400 MHz, CDCl$_3$) δ 7.48-7.40 (m, 5H), 7.30-7.26 (m, 2H), 7.22-7.18 (m, 3H), 5.93 (d, J=17.6 Hz, 1H), 5.82 (s, 1H), 4.21-4.15 (m, 2H), 2.70 (t, J=7.5 Hz, 2H), 2.46-2.41 (m, 2H), 2.04-1.98 (m, 2H), 1.37 (t, J=7.1 Hz, 3H).

EXAMPLE 7

Preparation of 2-ethoxy-4-phenyl-6-n-butyl-1,2-oxaphosphorin 2-oxide

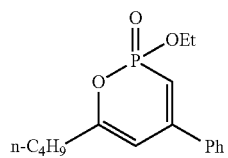

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen phenylethynylphosphonate (63.0 mg, 0.3 mmol) diluted with 0.5 mL of dichloroethane was added thereto, and finally, hex-1-yne (49.2 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-phenyl-6-n-butyl-1,2-oxaphosphorin 2-oxide (68.5 mg, 70%) which is a title compound.

$^1$H NMR (400 MHz, CDCl$_3$) δ 7.49-7.46 (m, 2H), 7.43-7.41 (m, 3H), 5.92 (d, J=16.4 Hz, 1H), 5.83 (s, 1H), 4.22-4.15 (m, 2H), 2.44-2.39 (m, 2H), 1.66-1.61 (m, 2H), 1.43-1.35 (m, 5H), 0.94 (t, J=7.4 Hz, 3H).

EXAMPLE 8

Preparation of 2-ethoxy-4-p-tolyl-6-n-butyl-1,2-oxaphosphorin 2-oxide

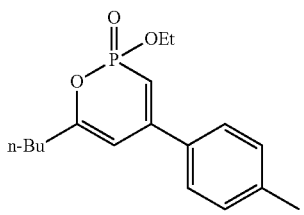

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen p-tolylethynylphosphonate (67.3 mg, 0.3 mmol) diluted with 0.5 mL of dichloroethane was added thereto, and finally, hex-1-yne (49.2 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-p-tolyl-6-n-butyl-1, 2-oxaphosphorin 2-oxide (68.5 mg, 70%) which is a title compound.

$^1$H NMR (400 MHz, CDCl$_3$) δ 7.37 (d, J=8.1 Hz, 2H), 7.22 (d, J=8.1 Hz, 2H), 5.89 (d, J=17.6 Hz, 1H), 5.82 (s, 1H), 4.21-4.13 (m, 2H), 2.43-2.38 (m, 2H), 2.38 (s, 3H), 1.66-1.60 (m, 2H), 1.43-1.34 (m, 5H), 0.94 (t, J=7.3 Hz, 3H).

EXAMPLE 9

Preparation of ethyl 5-chloropent-1-en-2-yl p-tolylethynylphosphonate

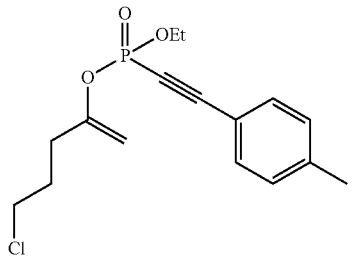 [SMILES: C=C(CCCCl)OP(=O)(C#Cc1ccc(C)cc1)OCC]

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) and triethylamine (Et$_3$N) (3.0 mg, 0.03 mmol) were put into a reaction container, and dichloroethane (0.4 mL) was put thereinto. After stirring at room temperature for 5 minutes, ethyl hydrogen p-tolylethynylphosphonate (67.3 mg, 0.3 mmol) diluted with 0.5 mL of dichloroethane was added thereto, and finally, 5-chloropent-1-yne (61.5 mg, 0.6 mmol) was put thereinto. Then, when all of the starting materials disappeared in the TLC, the reaction was allowed to be completed. After the solvent was removed under low atmospheric pressure, the product was separated by chromatography to obtain ethyl 5-chloropent-1-en-2-yl p-tolylethynylphosphonate (68.5 mg, 70%) which is a title compound.

$^1$H NMR (400 MHz, CDCl$_3$) δ 7.56 (d, J=8.1 Hz, 2H), 7.19 (d, J=8.1 Hz, 2H), 5.0 (t, J=2.4 Hz, 1H), 4.66-4.65 (m, 1H), 4.28 (m, 2H), 3.60 (t, J=6.4 Hz, 2H), 2.44 (t, J=7.2 Hz, 2H), 2.39 (s, 3H), 2.07-2.01 (m, 2H), 1.43 (t, J=7.0 Hz, 3H).

EXAMPLE 10

Preparation of 2-ethoxy-4-p-tolyl-6-chloropropyl-1, 2-oxaphosphorin 2-oxide

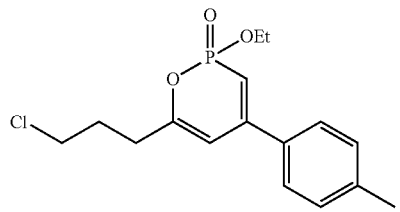 [SMILES: CCOP1(=O)C=C(c2ccc(C)cc2)C=C(CCCCl)O1]

Method 1—A gold (Ag(I)) catalyst {[Au(JohnPhos) NCCH$_3$]$^+$SbF$_6$—} [JohnPhos:(2-biphenyl)di-tent-butylphosphine] (11.3 mg, 0.015 mmol) was put into a reaction container, and dichloroethane (0.4 mL) was put thereinto. After stirring at room temperature for 5 minutes, ethyl 5-chloropent-1-en-2-yl p-tolylethynylphosphonate (Example 9, 97.8 mg, 0.3 mmol) diluted with 0.5 mL of dichloroethane was added thereto, and when all of the starting materials disappeared in the TLC, the reaction was allowed to be completed. After the solvent was removed under low atmospheric pressure, the product was separated by chromatography to obtain 2-ethoxy-4-p-tolyl-6-chloropropyl-1,2-oxaphosphorin 2-oxide (76.3 mg, 78%) which is a title compound.

Method 2—A gold (Ag(I)) catalyst {[Au(JohnPhos) NCCH$_3$]$^+$SbF$_6$—} [JohnPhos:(2-biphenyl)di-tent-butylphosphine] (11.3 mg, 0.015 mmol) was put into a reaction container, and dichloroethane (0.4 mL) was put thereinto. After stirring at room temperature for 5 minutes, ethyl hydrogen p-tolylethynylphosphonate (67.3 mg, 0.3 mmol) diluted with 0.5 mL of dichloroethane was added thereto, and finally, 5-chloropent-1-yne (61.5 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-p-tolyl-6-chloropropyl-1,2-oxaphosphorin 2-oxide (68.5 mg, 70%) which is a title compound.

$^1$H NMR (400 MHz, CDCl$_3$) δ 7.31 (d, J=8.1 Hz, 2H), 7.15 (d, J=8.1 Hz, 2H), 5.86 (d, J=17.1 Hz, 1H), 5.84 (s, 1H), 4.14-4.04 (m, 2H), 3.54 (t, J=6.3 Hz, 2H), 2.54-2.51 (m, 2H), 2.32 (s, 3H), 2.10-2.04 (m, 2H), 1.30 (t, J=7.1 Hz, 3H).

EXAMPLE 11

Preparation of (2-ethoxy-4-p-tolyl-1,2-oxaphosphorin 2-oxide-6-yl)methyl acetate

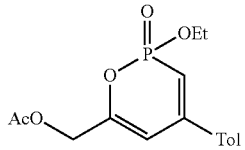

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen p-tolylethynylphosphonate (67.3 mg, 0.3 mmol) diluted with 0.5 mL of dichloroethane was added thereto, and finally, prop-2-ynyl acetate (129 mg, 1.5 mmol) was put thereinto. Then, when all of the starting materials disappeared in the TLC, the reaction was allowed to be completed. After the solvent was removed under low atmospheric pressure, the product was separated by chromatography to obtain (2-ethoxy-4-p-tolyl-1,2-oxaphosphorin 2-oxide-6-yl)methyl acetate (46.4 mg, 48%) which is a title compound.

$^1$H NMR (400 MHz, CDCl$_3$) δ 7.31 (d, J=8.1 Hz, 2H), 7.16 (d, J=8.1 Hz, 2H), 6.05 (s, 1H), 5.96 (d, J=17.1 Hz, 1H), 4.70 (s, 2H), 4.17-4.13 (m, 2H), 2.32 (s, 3H), 2.07 (s, 3H), 1.32 (t, J=7.1 Hz, 3H).

EXAMPLE 12

Preparation of 2-ethoxy-4-p-tolyl-6-(cyclohexylmethyl)-1,2-oxaphosphorin 2-oxide

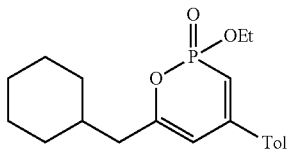

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen p-tolylethynylphosphonate (67.3 mg, 0.3 mmol) diluted with 0.5 mL of dichloroethane was added thereto, and finally, prop-2-ynylcyclohexane (73.2 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-p-tolyl-6-(cyclohexylmethyl)-1,2-oxaphosphorin 2-oxide (66.5 mg, 64%) which is a title compound.

$^1$H NMR (400 MHz, CDCl$_3$) δ 7.37 (d, J=8.2 Hz, 2H), 7.24 (d, J=8.2 Hz, 2H), 5.88 (d, J=17.6 Hz, 1H), 5.80 (s, 1H), 4.21-4.14 (m, 2H), 2.38 (s, 3H), 2.29-2.04 (m, 2H), 1.78-1.69 (m, 7H), 1.37 (t, J=7.1 Hz, 3H), 1.28-1.08 (m, 2H), 1.01-0.91 (m, 2H).

EXAMPLE 13

Preparation of 2-ethoxy-4-p-trifluoromethylphenyl-6-pentyl-1,2-oxaphosphorin 2-oxide

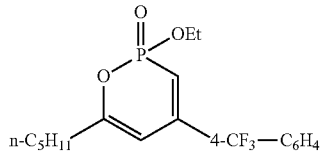

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen (4-(trifluoromethyl)phenyl)ethynylphosphonate (83.5 mg, 0.3 mmol) diluted with 0.5 mL of dichloroethane was added thereto, and finally, hept-1-yne (57.7 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-p-trifluoromethylphenyl-6-pentyl-1,2-oxaphosphorin 2-oxide (51.6 mg, 46%) which is a title compound.

$^1$H NMR (400 MHz, CDCl$_3$) δ 7.68 (d, J=8.2 Hz, 2H), 7.58 (d, J=8.2 Hz, 2H), 5.95 (d, J=16.8 Hz, 1H), 5.79 (s, 1H), 4.26-4.15 (m, 2H), 2.44-2.39 (m, 2H), 1.69-1.65 (m, 2H), 1.41-1.33 (m, 7H), 0.90 (t, J=7.1 Hz, 3H).

EXAMPLE 14

Preparation of 2-ethoxy-4-p-trifluoromethylphenyl-6-phenethyl-1,2-oxaphosphorin 2-oxide

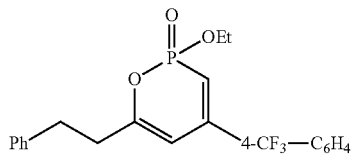

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen (4-(trifluoromethyl)phenyl)ethynylphosphonate (83.5 mg, 0.3 mmol) diluted with 0.5 mL of dichloroethane was added thereto, and finally, but-3-ynylbenzene (195 mg, 1.5 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-p-trifluoromethylphenyl-6-phenethyl-1,2-oxaphosphorin 2-oxide (45.3 mg, 37%) which is a title compound.

$^1$H NMR (400 MHz, CDCl$_3$) δ 7.65 (d, J=8.2 Hz, 2H), 7.49 (d, J=8.2 Hz, 2H), 7.33-7.29 (m, 2H), 7.24-7.20 (m, 3H), 5.96 (d, J=17.0 Hz, 1H), 5.70 (s, 1H), 4.27-4.20 (m, 2H), 2.99 (t, J=7.7 Hz, 2H), 2.74-2.70 (m, 2H), 1.40 (t, J=7.1 Hz, 3H).

EXAMPLE 15

Preparation of 2-ethoxy-4-n-butyl-6-cyclohexyl-1,2-oxaphosphorin 2-oxide

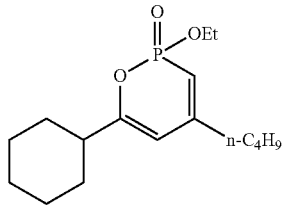

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen hex-1-ynylphosphonate (57.0 mg, 0.3 mmol) diluted with 0.5 mL of dichloroethane was added thereto, and finally, ethynylcyclohexane (64.9 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-n-butyl-6-cyclohexyl-1,2-oxaphosphorin 2-oxide (42.1 mg, 47%) which is a title compound.

$^1$H NMR (400 MHz, CDCl$_3$) δ 5.52 (d, J=19.4 Hz, 1H), 5.33 (s, 1H), 4.12-4.04 (m, 2H), 2.25 (t, J=7.5 Hz, 2H), 2.25-2.17 (m, 1H), 1.91-1.79 (m, 5H), 1.51-1.45(m, 2H), 1.37-1.17 (m, 10H), 0.92 (t, J=7.2 Hz, 3H).

EXAMPLE 16

Preparation of 2-ethoxy-4-n-butyl-6-n-butyl-1,2-oxaphosphorin 2-oxide

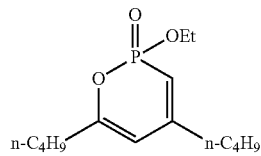

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen hex-1-ynylphosphonate (57.0 mg, 0.3 mmol) diluted with 0.5 mL of dichloroethane was added thereto, and finally, hex-1-yne (49.2 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-n-butyl-6-n-butyl-1,2-oxaphosphorin 2-oxide (53.1 mg, 65%) which is a title compound.

$^1$H NMR (400 MHz, CDCl$_3$) δ 5.53 (d, J=10.2 Hz, 1H), 5.36 (s, 1H), 4.14-4.06 (m, 2H), 2.34-2.26 (m, 2H), 2.24 (t, J=6.9 Hz, 2H), 1.60-1.47 (m, 4H), 1.39-1.31(m, 7H), 0.94-0.90 (m, 6H).

EXAMPLE 17

Preparation of 5-chloropent-1-en-2yl ethylhex-1-ynylphosphonate

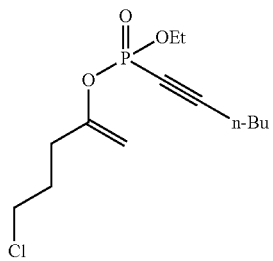

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) and triethylamine (Et$_3$N) (3.0 mg, 0.03 mmol) were put into a reaction container, and dichloroethane (0.4 mL) was put thereinto. After stirring at room temperature for 5 minutes, ethyl hydrogen hex-1-ynylphosphonate (57.0 mg, 0.3 mmol) diluted with 0.5 mL of dichloroethane was added thereto, and finally, 5-chloropent-1-yne (61.5 mg, 0.6 mmol) was put thereinto. Then, when all of the starting materials disappeared in the TLC, the reaction was allowed to be completed. After the solvent was removed under low atmospheric pressure, the product was separated by chromatography to obtain 5-chloropent-1-en-2yl ethylhex-1-ynylphosphonate (56.1 mg, 64%) which is a title compound.

$^1$H NMR (400 MHz, CDCl$_3$) δ 4.95 (t, J=2.3 Hz, 1H), 4.61 (s, 1H), 4.24-4.16 (m, 2H), 3.59 (t, J=6.3 Hz, 2H), 2.42-2.33 (m, 4H), 2.02-1.99 (m, 2H), 1.60-1.55 (m, 2H), 1.44-1.37 (m, 5H), 0.93(t, J=7.2 Hz, 3H).

EXAMPLE 18

Preparation of 2-ethoxy-4-n-butyl-6-3-chlorpropyl-1,2-oxaphosphorin 2-oxide

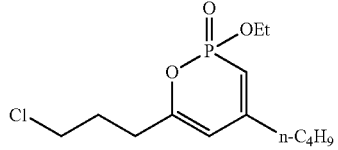

Method 1—A gold (Ag(I)) catalyst {[Au(JohnPhos)NCCH$_3$]$^+$SbF$_6$—} [JohnPhos:(2-biphenyl)di-tent-butylphosphine] (11.3 mg, 0.015 mmol) was put into a reaction container, and dichloroethane (0.4 mL) was put thereinto. After stirring at room temperature for 5 minutes, 5-chloropent-1-en-2yl ethylhex-1-ynylphosphonate (Example 17, 87.6 mg, 0.3 mmol) diluted with 0.5 mL of dichloroethane was added thereto, and when all of the starting materials disappeared in the TLC, the reaction was allowed to be completed. After the solvent was removed under low atmospheric pressure, the product was separated by chromatography to obtain 2-ethoxy-4-n-butyl-6-3-chlorpropyl-1,2-oxaphosphorin 2-oxide (82.3 mg, 94%) which is a title compound.

Method 2—A gold (Ag(I)) catalyst {[Au(JohnPhos)NCCH$_3$]$^+$SbF$_6$—} [JohnPhos:(2-biphenyl)di-tent-butylphosphine] (11.3 mg, 0.015 mmol) was put into a reaction container, and dichloroethane (0.4 mL) was put thereinto. After stirring at room temperature for 5 minutes, ethyl hydrogen hex-1-ynylphosphonate (57.0 mg, 0.3 mmol) diluted with 0.5 mL of dichloroethane was added thereto, and finally, 5-chloropent-1-yne (61.5 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-n-butyl-6-3-chlorpropyl-1,2-oxaphosphorin 2-oxide (56.1 mg, 64%) which is a title compound.

$^1$H NMR (400 MHz, CDCl$_3$) δ 5.57 (d, J=19.5 Hz, 1H), 5.44 (s, 1H), 4.17-4.11 (m, 2H), 3.57 (t, J=7.1 Hz, 2H), 2.55-2.44 (m, 2H), 2.25 (t, J=7.1 Hz, 2H), 2.11-2.04 (m, 2H), 1.53-1.43(m, 2H), 1.41-1.30 (m, 5H), 0.92 (t, J=7.1 Hz, 3H).

EXAMPLE 19

Preparation of 2-ethoxy-4-n-butyl-6-phenethyl-1,2-oxaphosphorin 2-oxide

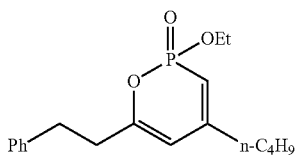

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen hex-1-ynylphosphonate (57.0 mg, 0.3 mmol) diluted with 0.5 mL of dichloroethane was added thereto, and finally, but-3-ynylbenzene (78 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-n-butyl-6-phenethyl-1,2-oxaphosphorin 2-oxide (64.4 mg, 67%) which is a title compound.

$^1$H NMR (400 MHz, CDCl$_3$) δ 7.31-7.26 (m, 2H), 7.22-7.17 (m, 3H), 5.55 (d, J=19.0 Hz, 1H), 5.29 (s, 1H), 4.16-4.08 (m, 2H), 2.92 (t, J=7.7 Hz, 2H), 2.63-2.58 (m, 2H), 2.22-2.18 (m, 2H), 1.47-1.39 (m, 2H), 1.35 (t, J=7.1 Hz, 3H), 1.35-1.25 (m, 2H), 0.90 (t, J=7.2 Hz, 3H).

EXAMPLE 20

Preparation of 2-ethoxy-4-n-butyl-6-3-phenylpropyl-1,2-oxaphosphorin 2-oxide

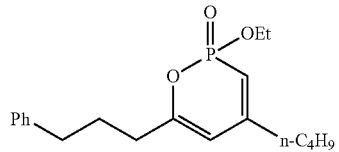

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen hex-1-ynylphosphonate (57.0 mg, 0.3 mmol) diluted with 0.5 mL of dichloroethane was added thereto, and finally, pent-4-ynylbenzene (86.5 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-n-butyl-6-3-phenylpropyl-1,2-oxaphosphorin 2-oxide (67.1 mg, 67%) which is a title compound.

$^1$H NMR (400 MHz, CDCl$_3$) δ 7.31-7.27 (m, 2H), 7.21-7.16 (m, 3H), 5.54 (d, J=9.2, 1H), 5.35 (s, 1H), 4.13-4.09 (m, 2H), 2.66(t, J=7.7 Hz, 2H), 2.36-2.30 (m, 2H), 2.26-2.22 (m, 4H), 1.95-1.92 (m, 2H), 1.50-1.46 (m, 2H), 1.37-1.31 (m, 5H), 0.92 (t, J=7.3 Hz, 3H).

EXAMPLE 21

Preparation of 2-ethoxy-4-p-chlorophenyl-6-n-butyl-1,2-oxaphosphorin 2-oxide

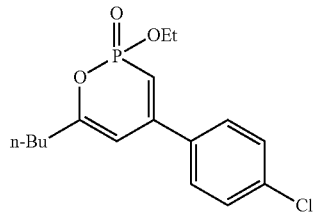

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen (4-chlorophenyl) ethynylphosphonate (73.4 mg, 0.3 mmol) diluted with 0.5 mL of dichloroethane was added thereto, and finally, hex-1-yne (49.2 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-p-chlorophenyl-6-n-butyl-1,2-oxaphosphorin 2-oxide (41.1 mg, 42%) which is a title compound.

$^1$H NMR (400 MHz, CDCl$_3$) δ 7.43-7.38 (m, 4H), 5.89 (d, J=17.1, 1H), 5.78 (s, 1H), 4.22-4.18 (m, 2H), 2.44-2.39(m, 2H), 1.66-1.62 (m, 2H), 1.42-1.36 (m, 5H), 0.94 (t, J=7.3 Hz, 3H).

EXAMPLE 22

Preparation of 2-ethoxy-4-p-chlorophenyl-6-(3-chloropropyl)-1,2-oxaphosphorin 2-oxide

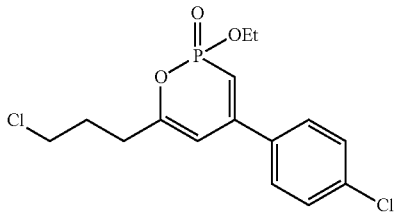 [SMILES: CCOP1(=O)C=C(c2ccc(Cl)cc2)C=C(CCCCl)O1]

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) was put into a reaction container, and dichloroethane (0.4 mL) was put thereinto. After stirring at room temperature for 5 minutes, ethyl hydrogen (4-chlorophenyl)ethynylphosphonate (73.4 mg, 0.3 mmol) diluted with 0.5 mL of dichloroethane was added thereto, and finally, 5-chloropent-1-yne (61.5 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-p-chlorophenyl-6-(3-chloropropyl)-1,2-oxaphosphorin 2-oxide (51.0 mg, 49%) which is a title compound.

$^1$H NMR (400 MHz, CDCl$_3$) δ 7.42-7.38 (m, 4H), 5.94 (d, J=17.1, 1H), 5.86 (s, 1H), 4.24-4.20 (m, 2H), 3.63-3.60 (m, 2H), 2.69-2.54(m, 2H), 2.17-2.11 (m, 2H), 1.39 (t, J=7.1 Hz, 3H).

EXAMPLE 23

Preparation of ethyl 5-phenylpent-1-en-2-yl 2-(4-chlorophenyl)ethynylphosphonate

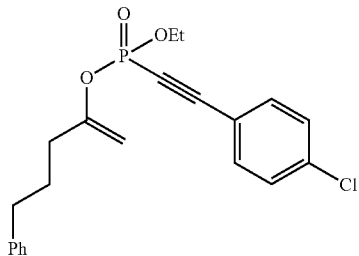 [SMILES: C=C(CCCc1ccccc1)OP(=O)(C#Cc1ccc(Cl)cc1)OCC]

A gold (Ag(I)) catalyst {[Au(JohnPhos)NCCH$_3$]$^+$SbF$_6$—} [JohnPhos:(2-biphenyl)di-tert-butylphosphine] (11.3 mg, 0.015 mmol) and triethylamine (Et$_3$N) (3.0 mg, 0.03 mmol) were put into a reaction container, and dichloroethane (0.4 mL) was put thereinto. After stirring at room temperature for 5 minutes, ethyl hydrogen (4-chlorophenyl)ethynylphosphonate (73.4 mg, 0.3 mmol) diluted with 0.5 mL of dichloroethane was added thereto, and finally, pent-4-ynylbenzene (86.5 mg, 0.6 mmol) was put thereinto. Then, when all of the starting materials disappeared in the TLC, the reaction was allowed to be completed. After the solvent was removed under low atmospheric pressure, the product was separated by chromatography to obtain ethyl 5-phenylpent-1-en-2-yl 2-(4-chlorophenyl)ethynylphosphonate (51.2 mg, 44%) which is a title compound.

$^1$H NMR (400 MHz, CDCl$_3$) δ 7.44 (d, J=1.8 Hz, 2H), 7.34 (d, J=1.7 Hz, 2H), 7.27-7.25 (m, 2H), 7.19-7.17 (m, 3H), 4.99 (t, J=2.3 Hz, 1H), 4.61 (s, 1H), 4.29-4.25 (m, 2H), 2.69-2.65 (m, 2H), 2.29 (t, J=7.4 Hz, 2H), 1.91-1.75 (m, 2H), 1.40 (t, J=7.1 Hz, 3H).

EXAMPLE 24

Preparation of 2-ethoxy-4-p-chlorophenyl-6-3-phenylpropyl-1,2-oxaphosphorin 2-oxide

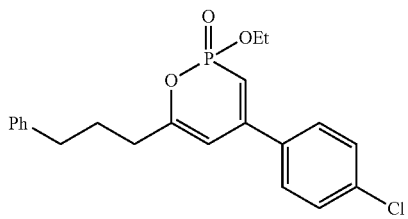 [SMILES: CCOP1(=O)C=C(c2ccc(Cl)cc2)C=C(CCCc2ccccc2)O1]

Method 1—A gold (Ag(I)) catalyst {[Au(JohnPhos)NCCH$_3$]$^+$SbF$_6$—} [JohnPhos:(2-biphenyl)di-tent-butylphosphine] (11.3 mg, 0.015 mmol) was put into a reaction container, and dichloroethane (0.4 mL) was put thereinto. After stirring at room temperature for 5 minutes, ethyl 5-phenylpent-1-en-2-yl 2-(4-chlorophenyl)ethynylphosphonate (Example 23, 116 mg, 0.3 mmol) diluted with 0.5 mL of dichloroethane was added thereto, and when all of the starting materials disappeared in the TLC, the reaction was allowed to be completed. After the solvent was removed under low atmospheric pressure, the product was separated by chromatography to obtain 2-ethoxy-4-p-chlorophenyl-6-3-phenylpropyl-1,2-oxaphosphorin 2-oxide (83.3 mg, 72%) which is a title compound.

Method 2—A gold (Ag(I)) catalyst {[Au(JohnPhos)NCCH$_3$]$^+$SbF$_6$—} [JohnPhos:(2-biphenyl)di-tent-butylphosphine] (11.3 mg, 0.015 mmol) was put into a reaction container, and dichloroethane (0.4 mL) was put thereinto. After stirring at room temperature for 5 minutes, ethyl hydrogen (4-chlorophenyl) ethynylphosphonate (73.4 mg, 0.3 mmol) diluted with 0.5 mL of dichloroethane was added thereto, and finally, pent-4-ynylbenzene (86.5 mg, 0.6 mmol) was put thereinto. Then, when all of the starting materials disappeared in the TLC, the reaction was allowed to be completed. After the solvent was removed under low atmospheric pressure, the product was separated by chromatography to obtain 2-ethoxy-4-p-chlorophenyl-6-3-phenylpropyl-1,2-oxaphosphorin 2-oxide (65.2 mg, 56%) which is a title compound.

$^1$H NMR (400 MHz, CDCl$_3$) δ 7.42-7.38 (m, 4H), 7.32-7.27 (m, 2H), 7.22-7.18 (m, 3H), 5.91 (d, J=17.1, 1H), 5.76 (s, 1H), 4.24-4.09 (m, 2H), 2.68(t, J=7.7, 2H), 2.45-2.41 (m, 2H), 2.04-1.96 (m, 2H), 1.37 (t, J=7.0, 3H).

The invention claimed is:

1. A phosphorus 2-pyrone derivative represented by the following Chemical Formula 1:

[Chemical Formula 1]

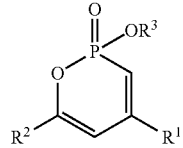

in Chemical Formula 1,
R$^1$ is (C1-C7)alkyl or (C6-C20)aryl;
R$^2$ is (C1-C7)alkyl, (C3-C12)cycloalkyl, (C6-C20)aryl, (C3-C12)cycloalkenyl or (C6-C20)ar(C1-C7)alkyl;
R$^3$ is (C1-C7)alkyl; and the alkyl and the aryl of R[1] and R[2] may be further substituted with one or more selected from the group consisting of halogen, (C1-C7)alkyl, halo(C1-C7)alkyl, (C3-C12)cycloalkyl and (C1-C7)alkylcarbonyloxy.

2. The phosphorus 2-pyrone derivative of claim 1, wherein R[1] is n-butyl, n-pentyl, phenyl, 4-methylphenyl, 4-chlorophenyl or 4-trifluoromethylphenyl; R[2] is n-butyl, n-pentyl, 1-bromoethyl, 1-chloropropyl, cyclohexyl, cyclohexenyl, phenyl, 4-methylphenyl, 4-chlorophenyl, 4-trifluoromethylphenyl, 1-phenylethyl, 1-phenylpropyl, methylcarbonyloxymethyl, benzyl or cyclohexylmethyl; and R[3] is methyl, ethyl, propyl, butyl, pentyl hexyl or heptyl.

3. The phosphorus 2-pyrone derivative of claim 2, wherein it is selected from the following compounds:

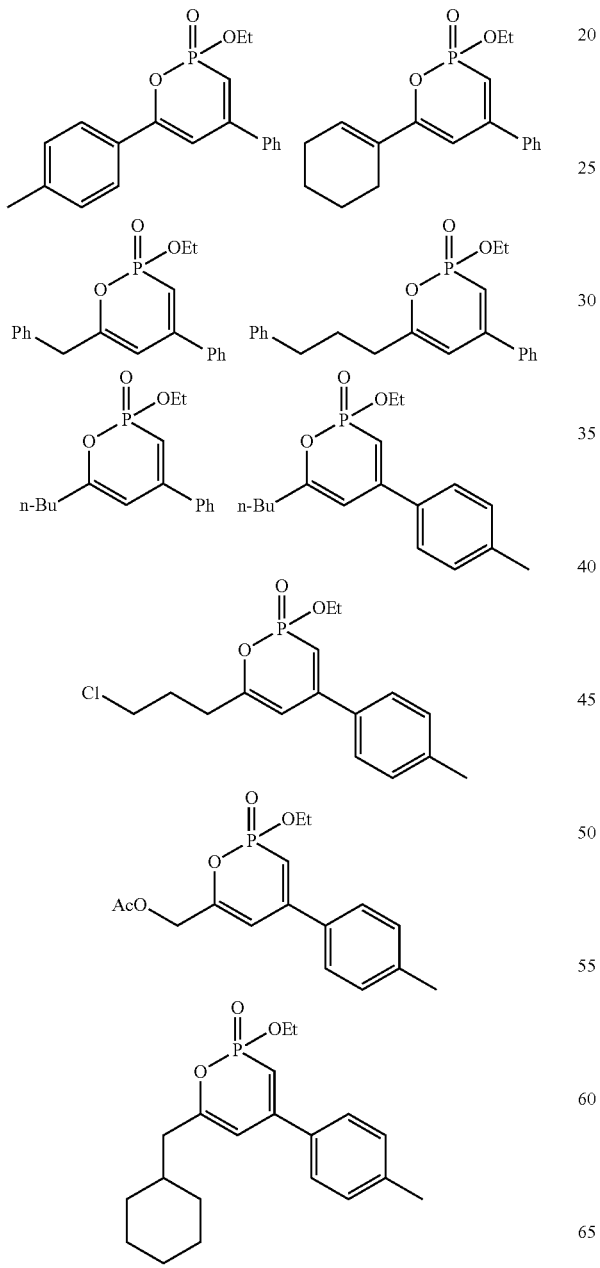

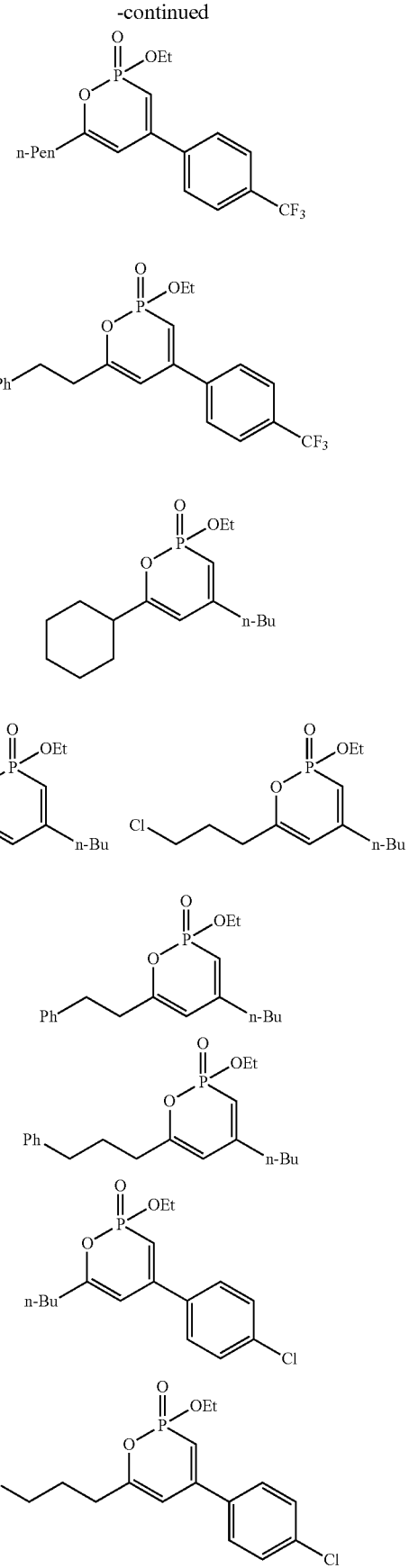

-continued

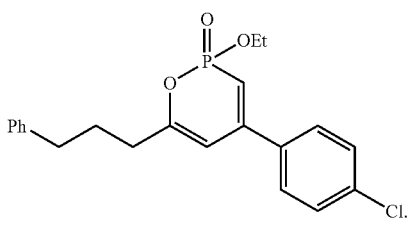

4. An alkyl alkenyl alkynyl phosphonate derivative represented by the following Chemical Formula 2:

[Chemical Formula 2]

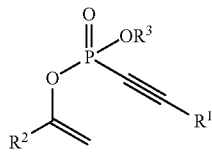

in Chemical Formula 2,
- $R^1$ is (C1-C7)alkyl or (C6-C20)aryl;
- $R^2$ is (C1-C7)alkyl, (C3-C12)cycloalkyl, (C6-C20)aryl, (C3-C12)cycloalkenyl or (C6-C20)ar(C1-C7)alkyl;
- $R^3$ is a (C1-C7)alkyl; and
- the alkyl and the aryl of $R^1$ and $R^2$ may be further substituted with one or more selected from the group consisting of halogen, (C1-C7)alkyl, halo(C1-C7)alkyl, (C3-C12)cycloalkyl and (C1-C7)alkylcarbonyloxy;
- provided that $R^1$ and $R^2$ are not the same as each other.

5. The alkyl alkenyl alkynyl phosphonate derivative of claim 4, wherein $R^1$ is n-butyl, n-pentyl, phenyl, 4-methylphenyl, 4-chlorophenyl or 4-trifluoromethylphenyl; $R^2$ is n-butyl, n-pentyl, 1-bromoethyl, 1-chloropropyl, cyclohexyl, cyclohexenyl, phenyl, 4-methylphenyl, 4-chlorophenyl, 4-trifluoromethylphenyl, 1-phenylethyl, 1-phenylpropyl, methylcarbonyloxymethyl, benzyl or cyclohexylmethyl; and $R^3$ is methyl, ethyl, propyl, butyl, pentyl, hexyl or heptyl.

6. The alkyl alkenyl alkynyl phosphonate derivative of claim 5, wherein it is selected from the following compounds:

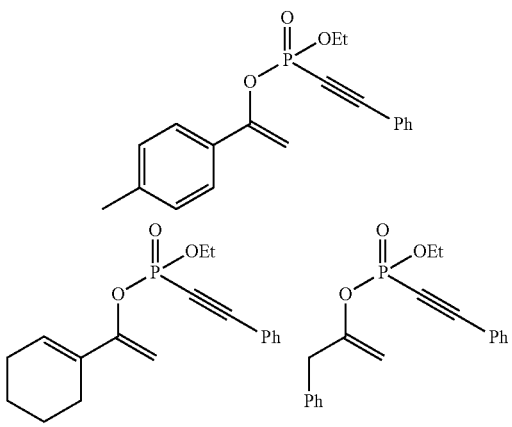

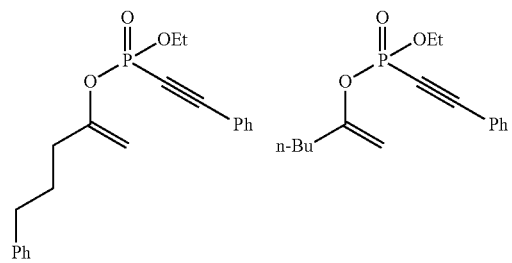

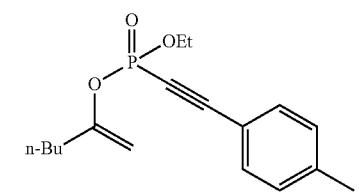

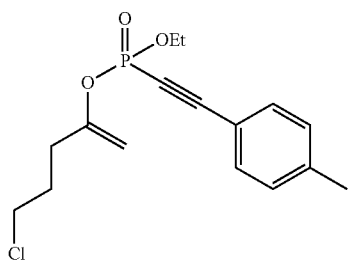

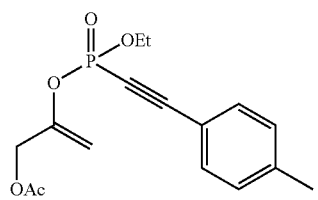

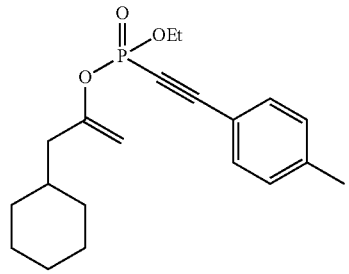

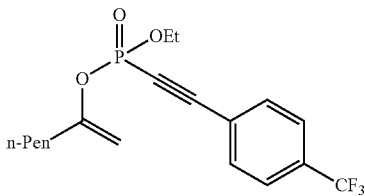

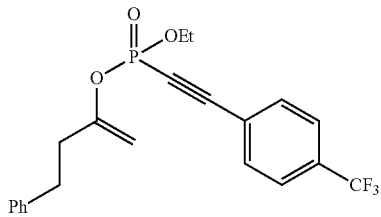

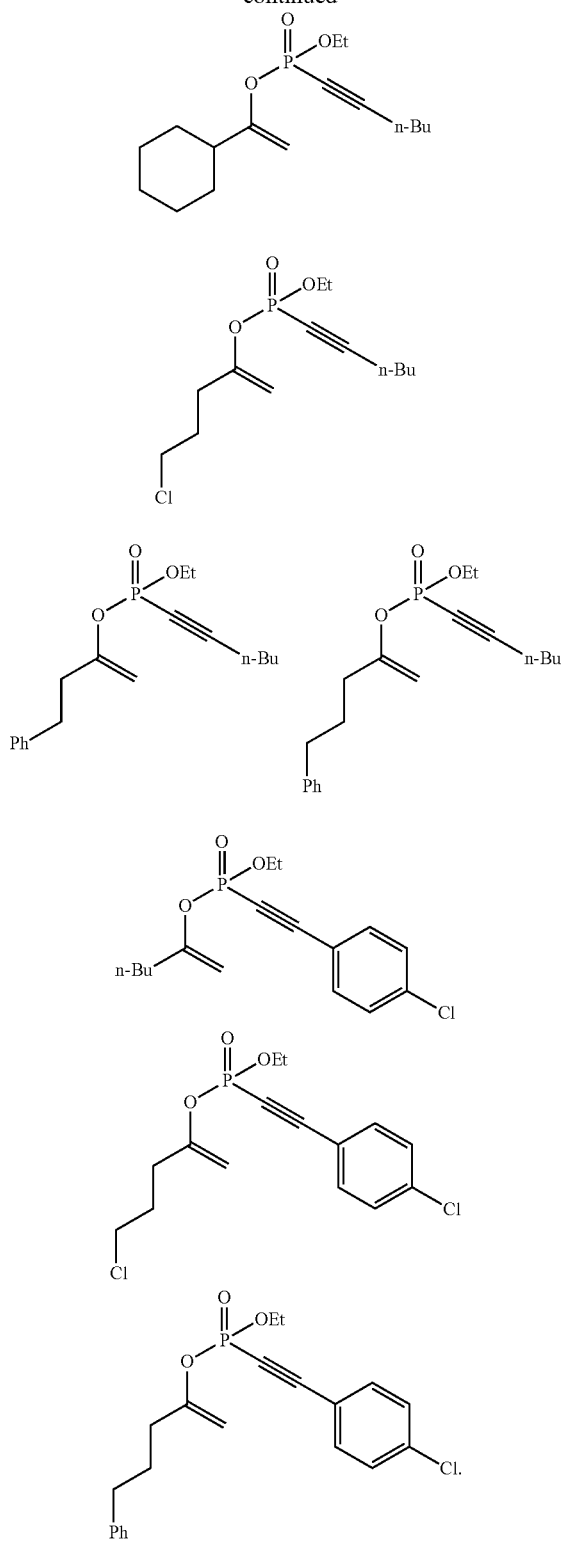

7. A preparation method of a phosphorus 2-pyrone derivative represented by the following Chemical Formula 1 by reacting an alkyl hydrogen alkynyl phosphonate derivative represented by the following Chemical Formula 3 and an alkyne derivative represented by the following Chemical Formula 4 in the presence of a gold catalyst:

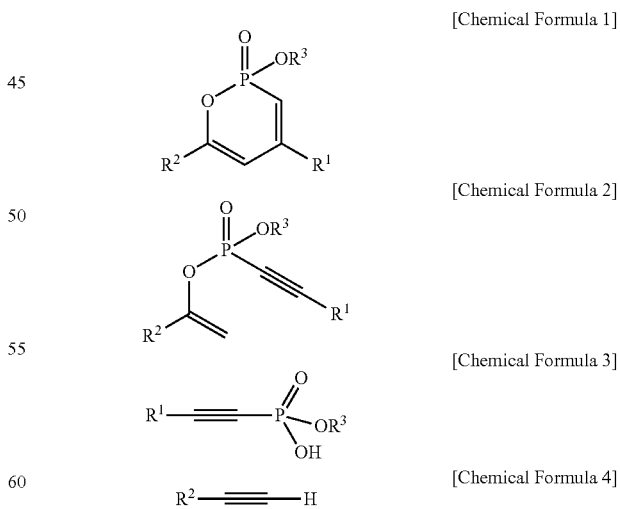

in Chemical Formulas 1, 3 and 4,
  $R^1$ is (C1-C7)alkyl or (C6-C20)aryl;
  $R^2$ is (C1-C7)alkyl, (C3-C12)cycloalky,(C6-C20)aryl, (C3-C12)cycloalkenyl or (C6-C20)ar(C1-C7)alkyl;
  $R^3$ is a (C1-C7)alkyl; and
  the alkyl and the aryl of $R^1$ and $R^2$ may be further substituted with one or more selected from the group consisting of halogen, (C1-C7)alkyl, halo(C1-C7)alkyl, (C3-C12)cycloalkyl and (C1-C7)alkylcarbonyloxy.

8. The preparation method of claim 7, wherein the phosphorus 2-pyrone derivative represented by the following Chemical Formula 1 is prepared by 1) reacting the alkyl hydrogen alkynyl phosphonate derivative represented by the following Chemical Formula 3 and the alkyne derivative represented by the following Chemical Formula 4 in the presence of the gold catalyst and a base to prepare an alkyl alkenyl alkynyl phosphonate derivative represented by the following Chemical Formula 2; and 2) performing an intramolecular cyclization reaction on the prepared alkyl alkenyl alkynyl phosphonate derivative represented by the following Chemical Formula 2 in the presence of the gold catalyst to prepare the phosphorus 2-pyrone derivative represented by the following Chemical Formula 1:

in Chemical Formulas 1, 2, 3, and 4,
  $R^1$, $R^2$ and $R^3$ are the same as defined in claim 7.

9. The preparation method of claim 7, wherein the gold (Au) catalyst is one or more selected from the group consisting of AuCl, AuBr, AuCl$_3$, Ph$_3$PAuCl, (C$_6$F$_5$)$_3$PAuCl, (4—CF$_3$—C$_6$H$_4$)$_3$PAuCl, IMesAuCl [IMes: 1,3-bis(2,4,6-trimethylphenyl)imidazol-2-ylidene], IPrAuCl [IPr: 1,3-bis(2,6-diisopropylphenyl)imidazol-2-ylidene], Au(JohnPhos)Cl [JohnPhos : (2-biphenyl)di-tert-butylphosphine]and { [Au(JohnPhos)NCCH$_3$]$^+$SbF$_6$—}.

10. The preparation method of claim 9, wherein the gold (Au) catalyst is used in 0.01 to 0.1 mol based on 1 mol of the alkyl hydrogen alkynyl phosphonate derivative represented by Chemical Formula 3.

\* \* \* \* \*